(12) United States Patent
Liu

(10) Patent No.: US 10,172,941 B2
(45) Date of Patent: Jan. 8, 2019

(54) METHOD FOR SYNTHESIS OF SILICA COATED GRAPHENE FUNCTIONAL HYBRID MATERIAL

(71) Applicant: SHT Smart High-Tech AB, Göteborg (SE)

(72) Inventor: Johan Liu, Västra Frölunda (SE)

(73) Assignee: SHT SMART HIGH-TECH AB, Göteborg (SE)

( * ) Notice: Subject to any disclaimer, the term of this patent is extended or adjusted under 35 U.S.C. 154(b) by 17 days.

(21) Appl. No.: 15/327,676

(22) PCT Filed: Jul. 24, 2014

(86) PCT No.: PCT/SE2014/050904
§ 371 (c)(1),
(2) Date: Jan. 20, 2017

(87) PCT Pub. No.: WO2016/013963
PCT Pub. Date: Jan. 28, 2016

(65) Prior Publication Data
US 2017/0202967 A1    Jul. 20, 2017

(51) Int. Cl.
| | |
|---|---|
| *A61K 47/02* | (2006.01) |
| *C09C 1/46* | (2006.01) |
| *B01J 21/18* | (2006.01) |
| *B01J 21/08* | (2006.01) |
| *B01J 37/02* | (2006.01) |
| *B01J 35/02* | (2006.01) |
| *C01B 33/12* | (2006.01) |
| *C01B 33/18* | (2006.01) |
| *B01J 35/00* | (2006.01) |
| *C01B 32/23* | (2017.01) |

(52) U.S. Cl.
CPC .............. *A61K 47/02* (2013.01); *B01J 21/08* (2013.01); *B01J 21/18* (2013.01); *B01J 35/0006* (2013.01); *B01J 35/026* (2013.01); *B01J 37/0221* (2013.01); *C01B 32/23* (2017.08); *C01B 33/12* (2013.01); *C01B 33/18* (2013.01); *C09C 1/46* (2013.01); *C01P 2002/82* (2013.01); *C01P 2004/04* (2013.01); *C01P 2004/64* (2013.01); *C01P 2004/80* (2013.01); *C01P 2004/84* (2013.01)

(58) Field of Classification Search
None
See application file for complete search history.

(56) References Cited

U.S. PATENT DOCUMENTS

2013/0230709 A1* 9/2013 Zhou .................... H01G 11/36
428/219

OTHER PUBLICATIONS

Moa Emling, International Search Report, parent International Application No. PCT/SE2014/050904, Patent-och registeringsverket, Stockholm Sweden May 11, 2015.
Wendo Lu, Synthesis of functional SiO2-coated graphene oxide nanosheets decorated with Ag nanoparticles for H2O2 and glucose detection, Biosensors and Bioelectronics, vol. 26, Issue 12, Aug. 15, 2011, pp. 4791-4797, Amsterdam, NL.
Kou, Making silica nanoparticle-covered graphene oxide nanohybrids as general building blocks for large-area superhydrophilic coatings, Nanoscale, 2011, 3, 519-528, Accepted Oct. 15, 2010, London, UK.
Li, The situ preparation of silica nanoparticles on the surface of functionalized graphene nanoplatelets, Nanoscale Research Letters, Apr. 9, 2014, 9:172; London, UK.
Valentini, Deposition of amino-functionalized polyhedral oligomeric silsesquioxanes on graphene oxide sheets immobilized onto an amino-silane modified silicon surface, Journal of Materials Chemistry, 2012, 22, 6213-6217, Accepted Feb. 3, 20112, First published on the web Feb. 17, 2012, London, UK.

* cited by examiner

*Primary Examiner* — Bong-Sook Baek
(74) *Attorney, Agent, or Firm* — Babcock IP, PLLC

(57) ABSTRACT

A process for synthesis of silica coated graphene hybrid material comprising the steps of treating graphene oxide with ammonium ions to provide ammonium-activated graphene oxide; treating the ammonium-activated graphene oxide with a solution comprising silica precursors; and silane coupling agents that comprise functional groups, to provide self-assembly of silica nanoparticles on the surface of the ammonium-activated graphene oxide and covalent bonding between the nanoparticles and the surface to provide silica coated graphene oxide; and grafting of the functional groups on the surface of the silica coated graphene oxide to provide functionalized silica coated graphene oxide; and reducing the functionalized silica coated graphene oxide to provide functionalized silica coated graphene. Silica coated graphene hybrid material obtainable by this process.

13 Claims, 2 Drawing Sheets

METHOD FOR SYNTHESIS OF SILICA COATED GRAPHENE FUNCTIONAL HYBRID MATERIAL

FIELD OF INVENTION

The present invention relates to a process for synthesis of silica coated graphene hybrid material. The invention also relates to silica coated graphene hybrid material obtainable by the process, and to the use this material as filler for composite materials, for drug delivery, and as catalyst carrier.

BACKGROUND

Graphene, a two-dimensional (2-D) nanomaterial, which possesses nanoscale dimension in thickness only and microscale length in the plane, has attracted tremendous attention owing to its unique properties and large surface areas.

Potential applications in the fields of drug delivery and catalyst carrier as well as fillers for composite materials have shown its great value both in academic and industry areas.

Therefore, high-throughput production of graphene while maintaining its large surface areas without agglomeration becomes a critical problem.

Lots of efforts have been carried out on surface modification of graphene to improve its dispersion performance, such as surface coating to form hybrid materials and grafting functional groups on the surface of graphene.

However, the results were not good enough for large scale production.

SUMMARY

Hence, one object of the present invention is to provide an improved process for high-throughput production of graphene while maintaining its large surface areas without agglomeration, in particular such a process with results good enough for large scale production.

Thus, one aspect of the invention relates to a process for synthesis of silica coated graphene hybrid material comprising the steps of:
a) treating graphene oxide with ammonium ions to provide ammonium-activated graphene oxide;
b) treating the ammonium-activated graphene oxide with a solution comprising
   one or more silica precursor(s); and
   one or more silane coupling agent(s) that comprise(s) one or more functional group(s), to provide
   self-assembly of silica nanoparticles on the surface of the ammonium-activated graphene oxide and also covalent bonding between said nanoparticles and said surface to provide silica coated graphene oxide; and
   grafting of said functional group(s) on the surface of the silica coated graphene oxide to provide functionalized silica coated graphene oxide;
and
c) reducing the functionalized silica coated graphene oxide to provide functionalized silica coated graphene.

BRIEF DESCRIPTION OF THE DRAWINGS

The present invention will be described in closer detail in the following description, examples and attached drawings, in which.

The graphene sheet has an average size of about 5-10 μm.

A silica layer was deposited on the surface of graphene sheet and formed a mesoporous structure.

Figure 1:
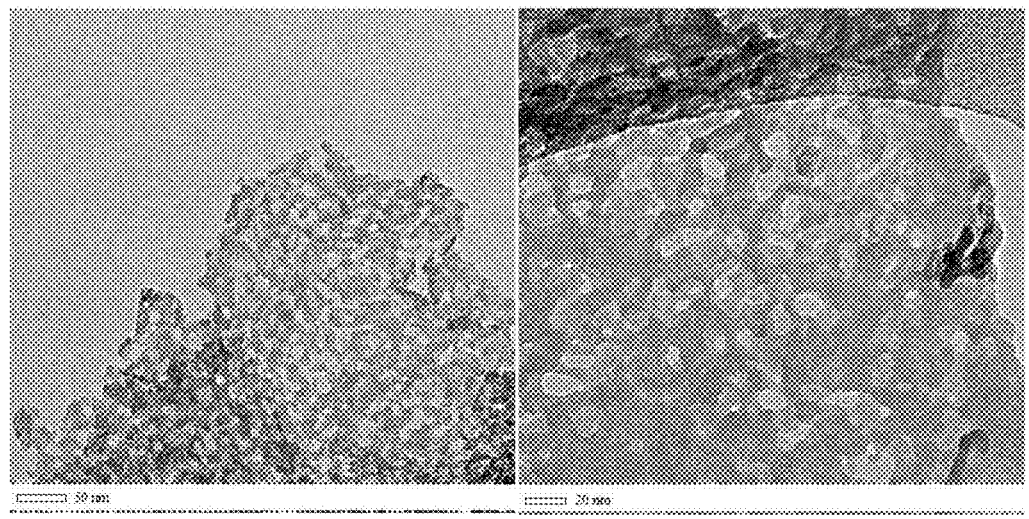
FIG. 1 shows Transmission Electron Microscopy (TEM) images, with different magnifications, of silica coated graphene hybrid material obtained by the inventive process.
Figure 2:
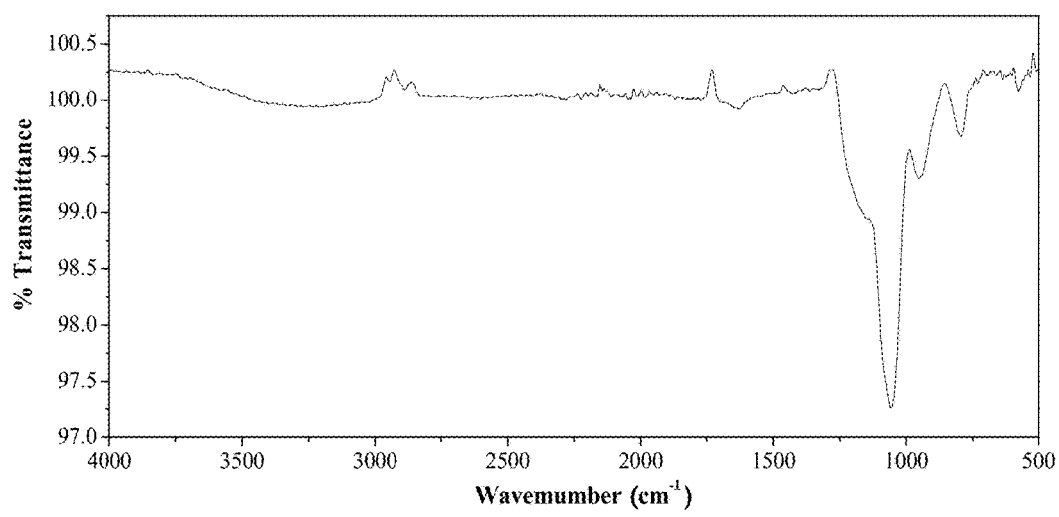

FIG. 2 shows a Fourier Transform Infrared Spectroscopy (FTIR) spectra of silica coated graphene hybrid material obtained by the inventive process.

The characteristic bands at about 1085, 800 and 460 $cm^{-1}$ correspond to the stretching, bending and out-of-plane bending of Si—O bonds respectively.

The position and the shape of the main Si—O vibrational band at 1085 $cm^{-1}$ in the FTIR spectra indicates a stoichiometric silicon dioxide structure.

The wide peak from 3000 to 3500 $cm^{-1}$ indicates the existence of functional group, in this case an amide group.

Figure 3:
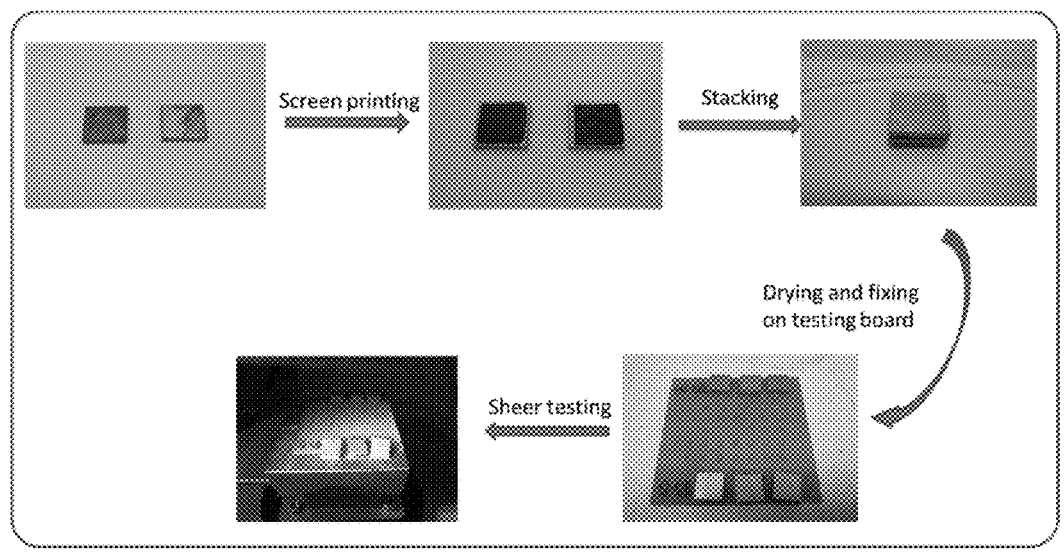

FIG. 3 shows a sketch of sample preparation and testing process performed as part of comparative tests between silica coated graphene hybrid material obtained by the inventive process, on the one hand, and prior art graphene hybrid material on the other hand.

DETAILED DESCRIPTION

Before the present invention is disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the claims, the singular forms "a", "an", and "the" include plural referents unless the context clearly dictates otherwise.

In this specification, unless otherwise stated, the term "about" modifying the quantity of a component in the process of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to carry out the process; and the like. The term "about" also encompasses amounts that differ due to different equilibrium conditions for a composition resulting from a particular initial mixture. Whether or not modified by the term "about", the claims include equivalents to the quantities.

In this specification, unless otherwise stated, the term "graphene" should be understood to include both pure graphene and graphene with small amounts of graphene oxide.

The present invention provides for large-scale production of highly-separated silica coated graphene hybrid material with functional groups, below referred to as fG@silica.

It specifically provides for both surface functionalization and coating into a single process.

The obtained silane functionalization on the graphene surface is provided by silane groups, which can significantly improve silica coating effect and amount by acting as connecting agents.

The surface functionalization does not only form covalent bonds between silica and graphene, but also provide extra functional groups for future combination of fG@silica with for instance polymers. Hence, those functional groups can enhance the binding force of fG@silica hybrid material with other substrates to give better mechanical performance.

The coating of silica nanoparticles on the graphene surface can, to a large extent, reduce and block Van der Waals' force between the graphene sheets. Consequently, the graphene sheets can be fully separated from each other.

Under microscopic observation, it has been found that the resulting fG@silica sheets possess:
  a large aspect ratio, about 500-1000 (diameter/thickness);
  a mesoporous silica structure;
  high surface area, about 300-1000 $m^2/g$; and
  high monodispersion capability.

These properties not only facilitate the separation of the graphene sheets in all kinds of solvents, but also provide for hosting of guest ions or guest molecules in many diffusion-controlled systems.

Compared with traditional silica coating process, the silica self-assembling process of the present invention shows great advantage in controlling the growth position and growth speed of silica.

The resulting fG@silica has much stronger mechanical properties and competitive advantages in refining and reinforcing the microstructure of composite materials due to covalent bonding instead of Van der Waals interactions.

In one embodiment the inventive process the ammonium ions are primary ammonium ions. The primary ammonium ions may, for instance, be obtained from, and/or originate from, an aqueous solution comprising ammonium sulfate, ammonium chloride, ammonium nitrate, or ammonium carbonate, or a combination thereof.

In one embodiment the inventive process the silica precursor is tetraethylorthosilicate (TEOS).

In one embodiment the inventive process the solution used in step b) additionally contains alkali. The alkali may, for instance, be sodium hydroxide or potassium hydroxide, or a combination thereof.

In one embodiment the inventive process the solution used in step b) additionally contains one or more organic solvent(s). The organic solvent(s) may, for instance, be chosen among ethanol, acetone, isopropanol, tetrahydrofuran, and combinations thereof.

In one embodiment the inventive process at least one of the one or more functional group(s) is a hydrolyzable group. The hydrolyzable group may, for instance, be chosen among alkoxy, acyloxy, amine, and chlorine.

In one embodiment the inventive process the treatment in step b) is carried out for a period of from about 2 to about 12 hours, specifically about from about 2 to about 6 hours.

In one embodiment the inventive process the treatment in step b) is carried out at a temperature of about 80 to 100° C.

In one embodiment the inventive process the pH during the treatment in step b) is controlled to be in the range of about 12-14.

In one embodiment the inventive process the reduction in step c) is carried out by means of one or more reducing agent(s) chosen among hydrazine hydrate, sodium borohydride, hydroiodic acid, Lewis acid, and combinations thereof.

Another aspect of the invention relates to silica coated graphene hybrid material obtainable by the inventive process.

Another aspect of the invention relates to use of the inventive silica coated graphene hybrid material as filler for composite materials.

Another aspect of the invention relates to use of the inventive silica coated graphene hybrid material for drug delivery.

Another aspect of the invention relates to use of the inventive silica coated graphene hybrid material as catalyst carrier.

The invention will be illustrated in closer detail in the following non-limiting examples.

EXAMPLES

Graphene oxide (GO) was synthesized from natural graphite flakes by following the modified Hummers method (described in Hummers W S, Offeman R E 1958 *J. Am. Chem. Soc.* 80, 1339).

0.5 g Ammonium chloride was slowly added into 100 ml of an aqueous GO suspension with a GO concentration of 10 mg/ml with mechanical stirring and then treated with ultra-sonication for 10 min.

By this treatment $NH_4^+$ was absorbed by the negatively charged GO. The resulting GO colloid with absorbed $NH_4^+$ ions (GO@$NH_4^+$) was separated from the solution by means of centrifugation and the redispersed into deionized water by means of ultrasonication.

The hence obtained GO@$NH_4^+$ dispersion was then treated with a silica self-assembling solution composed of 0.2 M tetraethylorthosilicate (TEOS), 8 mM 3-aminopropyl) triethoxysilane (APTES), 25 mM sodium hydroxide and ethanol.

Here, TEOS acted as the precursor of silica.

The silane coupling agents were used to build covalent bonding between GO and silica nanoparticles while providing extra functional groups for the final fG@silica.

The alkali was used to adjust the pH of the silica self-assembling solution to 12 in order to facilitate the hydrolyzation of TEOS and APTES.

The organic solvents were used for controlling the hydrolyzation speed of TEOS to prevent formation of independent silica nanoparticles in the solution.

Equal portions of the GO@$NH_4^+$ aqueous suspension and the silica self-assembling solution were mixed together.

The mixture was stirred at a temperature of about 25° C. for a period of 10 h.

After this treatment the obtained silica coated graphene hybrid with functional groups (fGO@silica) was cleaned by repeated washing and centrifugation with an ethanol-alcohol-water mixture.

The obtained fGO@silica colloid was then reduced in deionized water with strong reducing agents 2 g/l of L-ascorbic acid to get fG@silica colloid.

After final drying at a temperature of 80° C. in a vacuum oven, fG@silica dry powder is obtained.

COMPARATIVE EXAMPLES

A controlled experiment was designed to demonstrate the improved mechanical performance of the inventive fG@silica hybrid material in relation to a similar but non-functionalized material, below referred to as G@silica. The set-up of the experiment is outlined in FIG. 3.

A batch of an aqueous suspension of GO was divided into two equal portions.

One of these portions was treated as described in the above Example, while the other portion underwent a similar treatment, however without being treated with any silane coupling agents.

The fG@silica obtained from the first portion and the G@silica from the second portion were separated from the respective suspensions in the form of gelatinous precipitates by way of centrifugation.

A PET thin film with a thickness of 200 μm was patterned as a mask for screen printing of the silica coated materials.

Copper plates with dimensions of 8×8×1 mm were designed as testing substrates. fG@silica and G@silica were coated between two of these copper plates respectively.

After drying completely at 80° C. in a vacuum oven, the samples were transferred and fixed on a testing board.

Sheer strength measurements of the different samples were performed using a DAGE 4000 bond tester.

The results of these measurements are set forth in Table 1 below.

Three samples were tested for each material.

As is evident from these results, the samples with fG@silica have higher sheer strength the G@silica samples.

TABLE 1

Sheer testing results with different materials

| | Material | | | | | |
|---|---|---|---|---|---|---|
| | fG@silica | | | G@silica | | |
| Sample | 1 | 2 | 3 | 1 | 2 | 3 |
| Sheer strength/g | 76.3 | 100.4 | 84.7 | 1.7 | 0.4 | 2.0 |
| Average sheer strength/g | | 87.1 | | | 1.4 | |

Although the invention has been described with regard to certain embodiments it should be understood that various changes and modifications as would be obvious to one having the ordinary skill in this art may be made without departing from the scope of the invention as set forth in the claims appended hereto.

The invention claimed is:

1. A process for synthesis of silica coated graphene hybrid material comprising the steps of:
    a) treating graphene oxide with ammonium ions to provide ammonium-activated graphene oxide;
    b) treating the ammonium-activated graphene oxide with a solution comprising
        one or more silica precursor(s); and
        one or more silane coupling agent(s) that comprise(s) one or more functional group(s), to provide
            self-assembly of silica nanoparticles on the surface of the ammonium-activated graphene oxide and also covalent bonding between said nanoparticles and said surface to provide silica coated graphene oxide; and
            grafting of said functional group(s) on the surface of the silica coated graphene oxide to provide functionalized silica coated graphene oxide; and
    c) reducing the functionalized silica coated graphene oxide to provide functionalized silica coated graphene, wherein the ammonium ions are primary ammonium ions obtained from an aqueous solution comprising ammonium sulfate, ammonium chloride, ammonium nitrate, or ammonium carbonate, or a combination thereof.

2. The process according to claim 1, wherein the silica precursor is tetraethylorthosilicate (TEOS).

3. The process according to claim 1, wherein the solution used in step b) additionally contains alkali.

4. The process according to claim 3, wherein the alkali is sodium hydroxide or potassium hydroxide, or a combination thereof.

5. The process according to claim 1, wherein the solution used in step b) additionally contains one or more organic solvent(s).

6. The process according to claim 5, wherein the organic solvent(s) is/are chosen among ethanol, acetone, isopropanol, tetrahydrofuran, and combinations thereof.

7. The process according to claim 1, wherein at least one of said one or more functional group(s) is a hydrolyzable group.

8. The process according to claim 7, wherein said at least one hydrolyzable group is chosen among alkoxy, acyloxy, amine, and chlorine.

9. The process according to claim 1, wherein the treatment in step b) is carried out for a period of from about 2 to about 12 hours.

10. The process according to claim 9, wherein the period is from about 2 to about 6 hours.

11. The process according to claim 1, wherein the pH during the treatment in step b) is controlled to be in the range of about 12-14.

12. The process according to claim 1, wherein the reduction in step c) is carried out by means of one or more reducing agent(s) chosen among hydrazine hydrate, sodium borohydride, hydroiodic acid, Lewis acid, and combinations thereof.

13. Silica coated graphene hybrid material obtained by the process according to claim 1.

* * * * *